United States Patent
Borges

(10) Patent No.: US 9,904,765 B2
(45) Date of Patent: Feb. 27, 2018

(54) MONITORING MEDICAL DEVICE STATES TO DETERMINE UPDATE TIMING

(71) Applicant: CAREFUSION 303, INC., San Diego, CA (US)

(72) Inventor: Gregory Borges, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 45 days.

(21) Appl. No.: 14/153,995

(22) Filed: Jan. 13, 2014

(65) Prior Publication Data
US 2015/0199485 A1    Jul. 16, 2015

(51) Int. Cl.
| | |
|---|---|
| *G06F 9/445* | (2006.01) |
| *G06F 19/00* | (2018.01) |
| *A61M 5/168* | (2006.01) |
| *G05B 15/02* | (2006.01) |
| *A61M 5/142* | (2006.01) |
| *A61M 5/14* | (2006.01) |

(52) U.S. Cl.
CPC ......... *G06F 19/3406* (2013.01); *A61M 5/142* (2013.01); *A61M 5/168* (2013.01); *G05B 15/02* (2013.01); *G06F 19/3412* (2013.01); *A61B 2560/0209* (2013.01); *A61B 2560/029* (2013.01); *A61B 2560/0443* (2013.01); *A61M 5/1413* (2013.01); *A61M 5/1415* (2013.01); *A61M 2205/3553* (2013.01); *A61M 2205/3561* (2013.01); *A61M 2205/3569* (2013.01); *G06F 19/3468* (2013.01)

(58) Field of Classification Search
CPC .......... G06F 8/65; G06F 8/60; G06F 19/3412; G06F 11/1433; G06F 19/3468
See application file for complete search history.

(56) References Cited

U.S. PATENT DOCUMENTS

| | | | |
|---|---|---|---|
| 9,241,270 B1* | 1/2016 | Logue | G06F 8/65 |
| 2004/0103411 A1* | 5/2004 | Thayer | G06F 8/65 |
| | | | 717/171 |

(Continued)

OTHER PUBLICATIONS

Yang Cao et al., A Software Upgrade Method for Micro-electronics Medical Implants, IEEE, 2006, retrieved online on Sep. 2, 2017, pp. 5009-5012. Retrieved from the Internet: <URL: http://ieeexplore.ieee.org/stamp/stamp.jsp?arnumber=4462928>.*

*Primary Examiner* — Hanh T Bui
(74) *Attorney, Agent, or Firm* — Mintz Levin Cohn Ferris Glovsky and Popeo, P.C.

(57) ABSTRACT

A medical device operates in conjunction with a medical device controller. The medical device can include a low-power processor that monitors the states of the medical device. The low-power processor can determine to wake data processors and memory in the medical device based on the states. The data processors can further determine the current versions of executable code and configuration information associated with the data processors by polling a network server or a medical device controller to determine whether at least one update to the current versions is available. If an update is available, the medical device can receive the at least one update from the network server or medical device controller, and deploy it to the appropriate data processor. After deployment the medical device controller can activate the at least one update at a clinically appropriate time.

15 Claims, 6 Drawing Sheets

(56) References Cited

U.S. PATENT DOCUMENTS

| | | | |
|---|---|---|---|
| 2004/0240602 A1* | 12/2004 | Kim | G01D 5/28 377/16 |
| 2005/0110640 A1* | 5/2005 | Chung | G06K 7/10346 340/572.1 |
| 2008/0271010 A1* | 10/2008 | Sohoiler et al. | 717/168 |
| 2008/0301665 A1* | 12/2008 | Charlton | G06F 8/65 717/170 |
| 2010/0313105 A1* | 12/2010 | Nekoomaram | G06F 8/665 717/171 |
| 2011/0083445 A1* | 4/2011 | Heyd | F25B 21/04 62/3.3 |
| 2011/0289497 A1* | 11/2011 | Kiaie | G06F 8/65 717/171 |
| 2013/0104120 A1* | 4/2013 | Arrizza et al. | 717/173 |
| 2013/0253600 A1* | 9/2013 | Drew | G06F 19/3412 717/173 |
| 2014/0033002 A1* | 1/2014 | Nekoomaram | G06F 8/65 717/170 |
| 2014/0084688 A1* | 3/2014 | Tzanidis | H01F 38/14 307/42 |
| 2014/0276426 A1 | 9/2014 | Borges et al. | |
| 2015/0199485 A1* | 7/2015 | Borges | G06F 19/3406 700/90 |
| 2016/0041821 A1* | 2/2016 | Erickson | H04W 52/0212 717/171 |
| 2016/0128104 A1* | 5/2016 | Logue | G06F 8/65 370/329 |
| 2017/0223607 A1* | 8/2017 | Cho | H04W 40/246 370/255 |

\* cited by examiner

MONITORING MEDICAL DEVICE STATES TO DETERMINE UPDATE TIMING

TECHNICAL FIELD

The subject matter described herein relates to a modular medical device system. In particular, the current subject matter is directed to a system for coordinated operation of multiple medical devices such as infusion pumps and vital signs monitors including the updating of program and configuration information while the medical devices appear to be unpowered to a user or operator.

BACKGROUND

Medical device systems may utilize a plurality of different medical devices that are distinct stand-alone or independent medical devices. For example, some conventional infusion pumping systems may include up to about four functionally distinct stand-alone infusion pumps. Conventional infusion pumps are typically stand-alone complex devices that are only able to provide independent complex infusion functions. As such, collective coordination and control of the multiple devices is cumbersome.

Hospitals using several different models of pumps, where each pump employs a distinct user interface makes both learning and practicing their operation more time consuming and elevates the risk of error. For instance, there may be pumps for syringe, large volume, patient controlled analgesia, anesthesia and other uses. These difficulties can be compounded when there are other medical devices being used for patient care including various types of vital sign monitors and the like.

Further, many medical devices contain one or more programmable processors and memory with executable code and configuration information that must be updated from time to time. Coordination of updates across different medical devices and across multiple medical devices is important to reduce cost, to reduce the potential for treatment errors, and track to patient treatment.

SUMMARY

In one aspect, a medical device controller operates in conjunction with one or more medical devices. The medical device controller can include a low-power processor that monitors states of the medical device controller. The low-power processor can determine to wake at least one data processor and memory in the medical device controller from a low-power sleep condition based on the states. When awakened, the at least one data processor can determine one or more current versions of executable code and configuration information associated with the at least one data processor by polling a server to determine whether an update to the current versions of executable code and configuration information are available for the at least one data processor. If an update is available, the server can distribute the update to the medical device controller, and the medical device controller can deploy the update to an appropriate data processor in the controller. After deployment, the medical device controller can activate the update at a clinically appropriate time.

In an interrelated aspect, the states include a timer state, an accelerometer state, and/or a power source state. Periodically, the low-power processor determines to wake the at least one data processor and/or a communications interface. The timer state is used to determine when to wake the at least one data processor and/or a communications interface. The frequency of periodic waking is adjusted by adjusting the timer duration. For waking based on movement of the medical device controller, the accelerometer state is used to detect motion of the medical device controller. The power source state can be used to adjust the timer duration. When the battery charge level is low, the frequency of waking may be decreased to conserve power. When powered by an external source, the frequency of waking may be increased.

In another interrelated aspect, the clinically appropriate time to activate an update that has been distributed from a server to the medical device controller, and deployed to an appropriate data processor includes a time at least eight hours after the medical device controller has been turned off.

In another interrelated aspect, the waking comprises causing the at least one data processor and/or communications interface to exit the low-power condition by enabling the at least one data processor and associated memory, and/or at least one communications interface to operate.

In another related aspect, at least one communications interface can be operable to receive and transmit data from at least one remote computing system via a wired and/or wireless communication link. The at least one communications interface can also be operable to receive and transmit data from at least one medical device and/or medical device module via a wired or wireless connection.

In another aspect, a medical device operates in conjunction with a medical device controller. The medical device can include a low-power processor that monitors states of the medical device. The low-power processor can determine to wake at least one data processor and memory in the medical device from a low-power sleep condition based on the states. When awakened, the at least one data processor can determine one or more current versions of executable code and configuration information associated with the at least one data processor by polling the medical device controller and/or server to determine whether an update to the current versions of executable code and configuration information are available for the at least one data processor. If an update is available, the server can distribute the update to the medical device, and the medical device can deploy the update to an appropriate data processor in the medical device. After deployment, the medical device controller can activate the update at a clinically appropriate time.

A medical device module is a medical device that may couple into a modular medical device system. The modular medical device system may provide for inductive powering of the medical device module. Medical devices may also be stand-alone and not coupled into a modular system.

In another aspect, a medical device (or medical device module) receives at least one update including one or more of updated executable code and updated configuration information from a medical device controller for one or more processors in the medical device. The medical device further deploys the received update by determining the appropriate processor in the medical device associated with the update and transferring the update to an appropriate storage associated with the appropriate processor. The medical device further activates at a clinically appropriate time the deployed update by selecting to use the at least one update at the appropriate processor during operation of the medical device.

A wide variety of medical devices and medical device modules can be used in conjunction with the medical device controller. For example, the system can be used with infusion pumps such as syringe pumps, patient controlled infusion pumps (e.g., patient-controlled analgesia (PCA) system), large volume infusion pumps, peristaltic pumps, and the like. The medical device modules can also be one or more of a vital signs monitor, a cardiac output monitor, a gastric tonometer, an SpO2 sensor, an EtCO2 sensor, a blood analyte monitor, an identification module, a barcode scanner, and a radio frequency identification (RFID) scanner.

In another interrelated aspect, an infusion pump includes at least one data processor, memory storing instructions for execution by the at least one data processor, and at least one pumping sub-system for pumping fluid passing therethrough (via a tubing set, an IV cassette, etc.). Such an infusion pump can be configured such that it does not include an external electrical galvanic connector. In some variations, the infusion pump includes an inductive receiver for being inductively powered by an inductive backplane of a modular medical device system.

In a further interrelated aspect, a medical device includes at least one data processor, memory storing instructions for execution by the at least one data processor, and a housing. The housing may have a shape and size to be secured by an inductive backplane of a modular medical device system. A medical device module may also include an inductive receiver for powering medical device module. An inductive backplane may inductively power the inductive receiver when the housing of the medical device module is secured thereto.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection (wired or peer-to-peer wireless) between one or more of the computing systems, etc.

The subject matter described herein provides many advantages. For example, the current subject matter provides enhanced usability for clinicians both with regard to the ease of coupling and decoupling medical device modules (and medical devices that are not modules) from the system and in connection with the various user interfaces provided by the system. Further advantages include the coordinated distribution of updates to executable code and configuration information on a periodic basis and at times when the system and devices are not providing patient treatment which improves device availability and reliability. Updates to information such as the positions of a medical device can also be updated upon the detection of movement of the device which supports improved equipment tracking and patient treatment tracking. Coordinating executable code updates and configuration information updates assures compatibility of the configuration data and the executable code stored in a medical device. Moreover, when the processors in the medical device or system are updated together, operational compatibility between the processors can be assured. Furthermore, when all the medical devices in the system are updated together, compatibility between the medical devices in the system can also be assured. By coordinating the configuration information updates and executable code updates, the number of combinations of executable code versions and configuration information versions that must be tested to assure compatibility is reduced resulting in a more robust and reliable system. Also, by not re-sending updates of executable code or configuration information that medical devices have already received, time and bandwidth resources are conserved by eliminating unneeded or duplicate updates.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
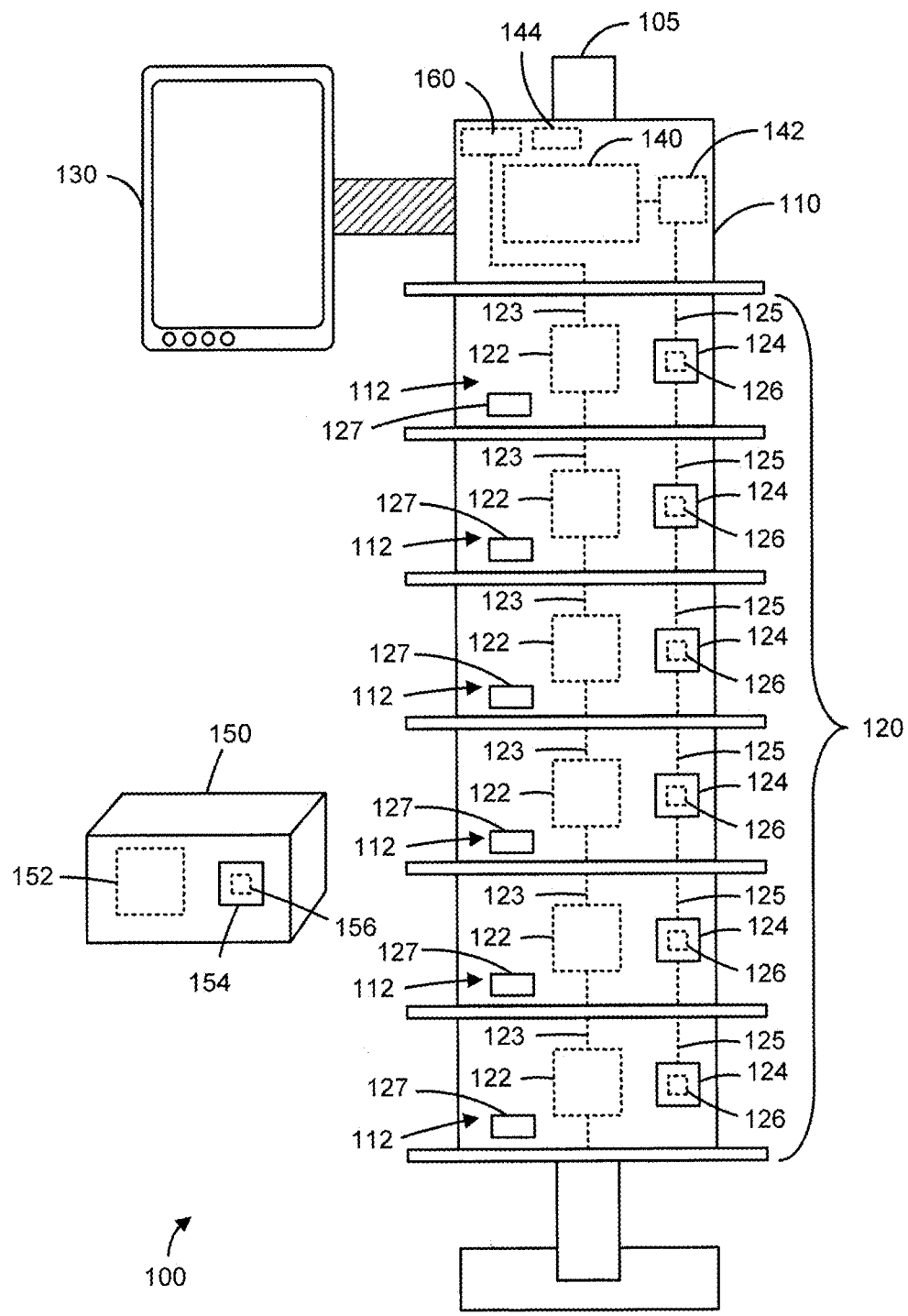
FIG. 1 is a diagram illustrating a modular medical device system.

FIG. 1 is a diagram 100 illustrating a modular medical device system 110. The system 110 comprises a backplane 120 that can be mounted on a pole 105. The backplane 120 can mechanically couple to and secure one or more medical device modules 150 (also referred to herein as a medical device) along each of a series of pre-defined mounting seats 112. In some variations, each of the mounting seats 112 are uniform in size and spacing, while in other variations different sizing and/or spacing can be used to accommodate medical device modules 150 having different exterior dimensions. In addition, the mounting seats 112 can be arranged along a single axis (e.g., a vertical axis as illustrated, etc.) or they can be arranged along two or more axes. The mounting seats 112 can each have one or more mechanical elements to detachably affix the medical device modules 150 to the backplane 120.

In addition to allowing the medical device modules to be affixed to the system, the backplane 120 can provide non-contact inductive power to one or more medical device modules 150. The backplane 120 can, for each mounting location, comprise an inductive transmitter 122 for non-contact powering of a medical device module 150. A corresponding inductive receiver 152 on the medical device module 150 can, when the medical device module 150 is affixed to the mounting seat 112, be inductively coupled with inductive transmitter 122 of backplane 120. In general, energy is sent via an inductive (magnetic) coupling between inductive transmitter 122 and inductive receiver 152. As a result, there is a wireless (no galvanic contact) energy transfer between inductive backplane 120 and medical device module 150. Moreover, an electrical galvanic connector, as is typical for powering conventional medical devices, is not required to provide power to medical device module 150. Use of non-contacting energy transfer avoids metallic contacts between medical device module 150 and a power source which may be damaged, require special cleaning and pose risk of electrical heating, smoke or fire. Each inductive transmitter 122 can be coupled to an induction bus 123 which in turn is connected to a power source 160 (e.g., a wired connection to an outlet, a battery, etc.) to enable the inductive coupling of each inductive transmitter 122.

Each mounting seat 112 can include a shelf with dove tail features extending from a housing of the system 110. Each medical device module 150 can include a latch mechanism on a top rear edge that affixes to the housing of the system 110. The latch mechanism can reduce load on the shelf and can cause the medical device module 150 to rotate back into contact with the system 110 under load (rather than deflect away from it). This arrangement can help insure that the inductive transmitter 122 is positioned properly and secured in relation to the inductive receiver 152.

Each mounting seat 112 can include a proximity sensor 127 that can detect the presence of a medical device module 150. The proximity sensors 127 can be optical, electric, electro-mechanical, and/or mechanical devices. For example, the proximity sensors 127 can comprise a Hall effect sensor and/or a mechanical switch. The presence of a medical device module 150 can be used to initiate, for example, inductive powering by the corresponding inductive transmitter 122 and/or communications via the communications interface 142. The proximity sensor 127 can also indicate an alarm condition when a medical device module 150 is not completely secured so that appropriate actions can be taken.

The backplane 120 can also provide an optical communications interface to one or more medical device modules 150 via respective optical communications ports 124 and optical transceivers 126 corresponding to each mounting seat 112. The medical device modules 150 can have corresponding optical communications ports 154 and optical transceiver 156 which can be optically aligned with the optical communication port 124 on the backplane 120 when the medical device module 150 is affixed to the backplane 120 so that a bi-directional data feed can be established between the optical transceivers 126, 156. Such data can relate to a variety of aspects including, but not limited to, data characterizing operation of the medical device module 150, data for controlling (e.g., modifying, monitoring, etc.) one more attributes of the medical device module 150 (e.g., updates to executable program code, configuration updates, asset locations, status information, historical data, patient information, patient treatment parameters, medication administration information, etc.), and the like. Executable program code that may be stored in memory and runs on a processor is sometimes referred to as software. The data exchanged via the optical transceivers 126, 156 can comprise any data generated or otherwise used by a medical device module 150 or a caregiver using same. The data transmitted to the backplane 120 can be consumed locally by the system 110 and/or it can be transmitted to one or more remote systems/devices coupled to the system 110 via a wired or wireless communications link. The optical data transceivers 126, 156 can be infrared (IR) data transceivers such that optical data 146 is propagated by IR light as the transmission medium. The optical data transceivers can be coupled to a communications bus 125 that in turn is coupled to a communications interface 142. The communications interface 142 can, in turn, be coupled to the control unit 140. In addition or in the alternative, a second communications interface 144 can provide an outward interface for the modular medical device system 110 that provides a wired or wireless connection to other devices and/or networks. It will be appreciated that any number of communications interfaces can be used, including one communications interface for each optical data transceiver 126/seat 112.

The control unit 140 can be hardware, software, or a combination of both. For example, the control unit 140 can be a specially designed hardware module including at least one processor and memory with specialized software (e.g. executable code) used to control any aspect of a medical device module 150 coupled to the system 110. In other cases, the control unit 140 can be a software module (or series of modules) used to control any aspect of a medical device module 150 coupled to the system 110. As used herein, unless otherwise specified, the term control shall relate to any type of data exchange with a medical device module 150 by the control unit 140 including data generated by a medical device module 150 and data used by a medical device module 150 (software updates, power state changes, etc.). For example, the control unit 140 can be used to selectively wake-up medical device modules 150 coupled to the inductive backplane 120 from a fully-off state (sometimes referred to as the "sleep state" or "sleep condition"). Furthermore, the control unit 140 can be coupled to one or more remote computing systems (via the communications interface 144) to allow for the remote control of the medical device modules 150.

In some implementations, the medical device module 150 and/or system 110 operate in at least three power states; a fully-off state, an active-off state, and a fully-on state (sometimes referred to as the "on-state"). In the fully-off state, the module 150 and/or system 110 appears to be powered down (dark display, no response to user input, no response noises, etc.), but a low-power processor continues to operate in order to monitor the internal states of the module 150 and/or system 110. The low-power processor determines when to initiate a transition to the active-off state based on a timer, an accelerometer, and power source status monitored by the low-power processor. When the low-power processor determines to initiate a transition to the active-off state, the low-power processor causes one or more data processors in the module 150 and/or system 110 to become active by powering them up or waking them from a sleep state. In the active-off state, the module 150 and/or system 110 still appears to a user/patient to be fully-off with no displays, lights, audio, and unresponsive to user actions (except the "on" button"). The one or more data processor have networking capability and can contact a server to determine whether there are updates waiting, or whether data should be sent to the server. The other processors can also update the location of the module 150/system 110 from a real time location system (RTLS). Updates to executable code and configuration information can be transferred from the server to the system 110 while the system 110 is in the active-off state, from the server to the module 150 while the module 150 is in the active-off state, and/or from the system 110 to the module 150 while the module 150 is in the active-off state. If the "on" button on the module 150 or system 110 is pressed, the low-power processor initiates a transition from either the fully-off state or the active-off state to the fully-on state. In the fully-on state the low-power processor and the other processors are active, the display is on, and the module 150 and/or system 110 will interact with a user/operator/patient Medical device module 150 can be any medical device that is compatible for scalability in a modular medical device system. For instance, the modular medical device system 110 can utilize one or more medical device modules 150 depending on the functionality that is needed for proper care of a patient. Moreover, a modular medical device system 110 can be scaled up to incorporate additional medical device modules 150 and also scaled down by removing medical device modules 150.

For example, if patient care requires only one infusion pump, then the modular medical device system 110 can include a single affixed infusion pump. Moreover, if patient care requires two infusion pumps, then the modular medical device system 110 can be scaled up to include an affixed additional infusion pump.

Medical device module 150 can include, but is not limited to, an infusion pump (e.g., a large volume pump (LVP), a syringe pump), a patient-controlled analgesia (PCA) system, a vital signs monitor (VSM) (e.g., an SpO2 sensor, an EtCO2 sensors, a cardiac output monitor, a gastric tonometer, etc.), a bedside blood analyte analyzer (e.g. blood glucose), an Auto-ID module (barcode scanner and RFID), and other devices which measure physiological parameters associated with a patient and/or assist with the clinical care of the patient (and such medical device modules 150 may not necessarily measure physiological parameters of the patient).

Modular medical device system 110 can also include a display unit 130 that provides a unified interface that characterizes the operation of various medical device modules 150 coupled to the backplane 120. The display unit 130 can include a touch screen interface that allows a user to selectively view and alter performance parameters/metrics of individual medical device modules 150, concurrently view performance parameters/metrics of multiple medical device modules 150, and additionally orchestrate complex sequences of infusions/operations from multiple medical device modules 150. The display unit 130 can be affixed to an outer housing of the modular medical device system 130/inductive backplane 120 by a tilt and swivel arm mount that allows the display unit to be moved on different sides of the system 110 and/or to change varying positions (to accommodate different positions/heights of caregivers).

The display unit 130 can include a speaker to provide audio cues relating to various aspects of medical device modules 150 (in other versions the speaker is located elsewhere in the system 110). When the medical device modules 150 are coupled to the backplane 120, audio cues such as alarms for such medical device modules 150 can be delegated so that the system 110 handles the alarms whether via an audio and/or visual cue in the display unit 130 or by an audio cue generated elsewhere in the system 110. In some cases, some alarms can be still be handled by a medical device module 150 while other alarms are handled by the system 110.

Figure 2:
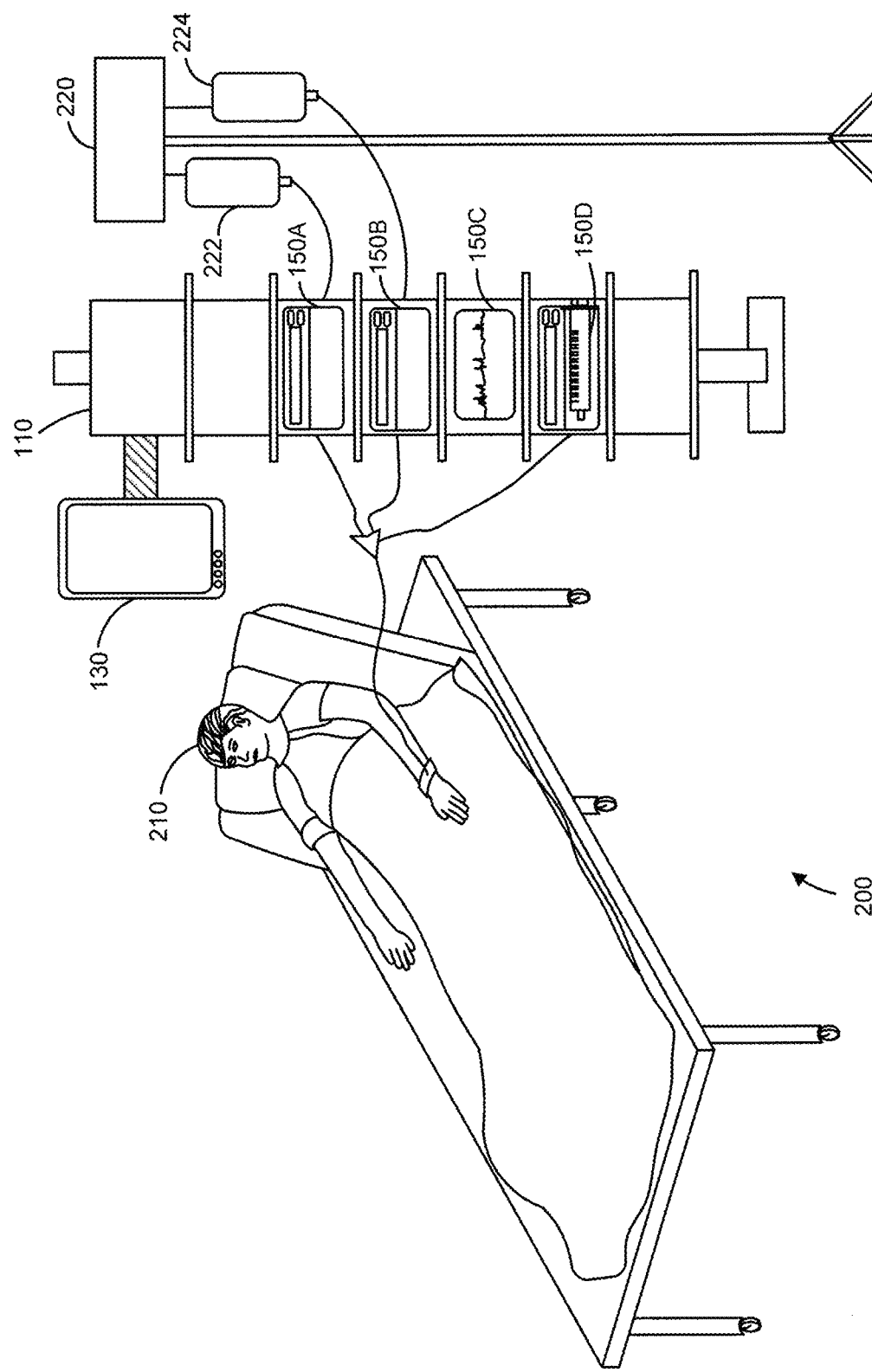
FIG. 2 is a diagram illustrating a modular medical device system in a clinical setting.

FIG. 2 is a diagram 200 illustrating a modular medical device system 110 in a clinical setting. In particular, in this view, the modular medical device system 110 is coupled to two infusion pumps 150A, 150B, a vital signs monitor 150C, and a syringe pump 150D. The infusion pumps 150A and 150B are respectively fluidically coupled to two fluid/medication containers 222, 224 suspended from an IV pole 220. In addition, each of the infusion pumps 150A and 150B and the syringe pump 150D are fluidically coupled to an IV catheter inserted into a patient 210 so that the corresponding fluids can be delivered to the patient. The modular medical device system 110 monitors and/or controls how fluids from the respective sources 150A, 150B, 150D are delivered to the patient 210. It will be appreciated that varying numbers of medical device modules 150 can be utilized depending on the particular condition of and/or treatment the patient 210.

Figure 3:
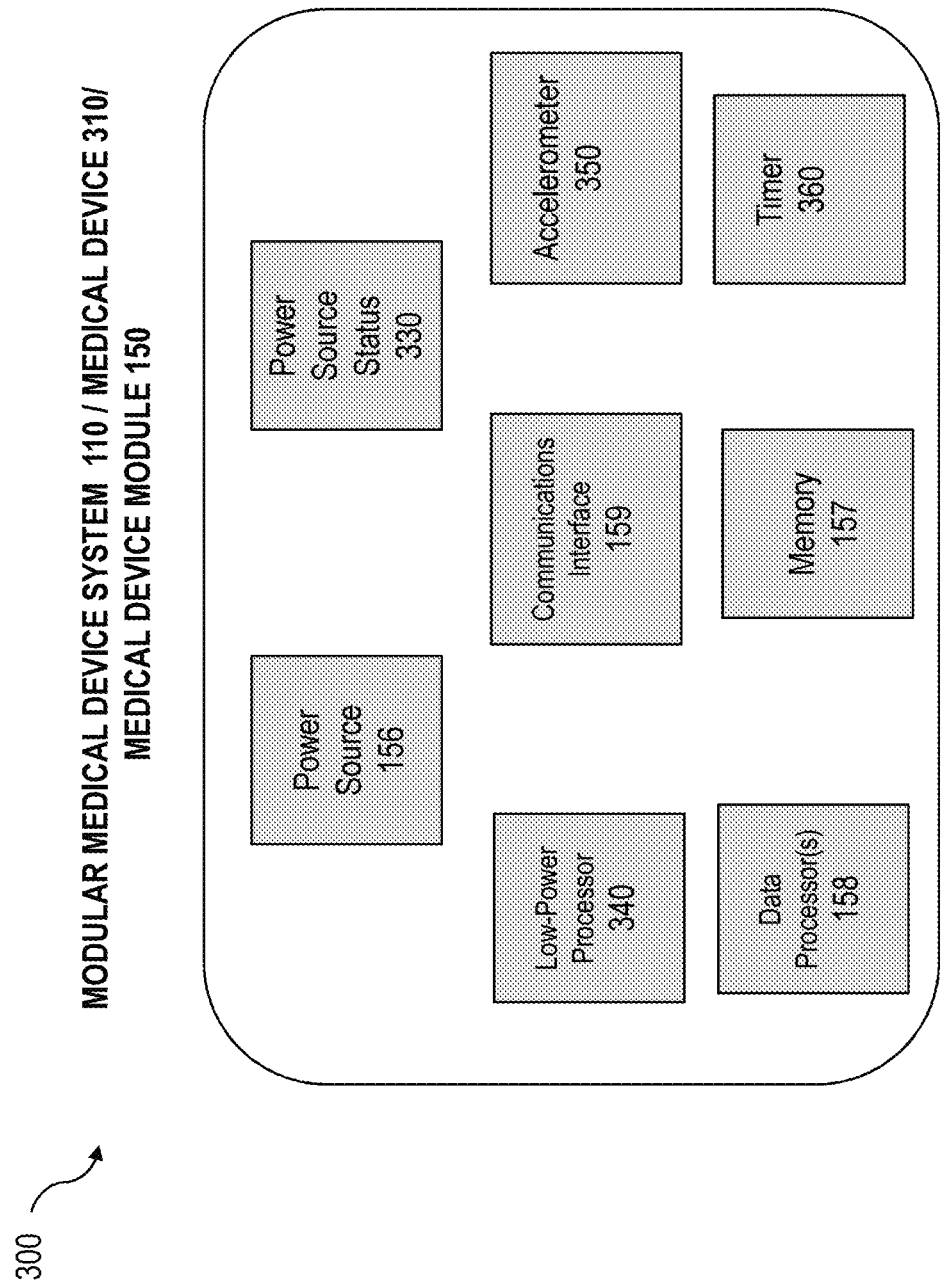
FIG. 3 is a logic diagram illustrating some components of a medical device, medical device module, and/or modular medical device system.

FIG. 3 is a logic diagram 300 showing components of a modular medical device system, medical device module/medical device consistent with some implementations. For example, the components can be included in a modular medical device system 110, included in a medical device module 150, and/or included in a medical device 310. For simplicity, the following description refers to the components of FIG. 3 being included in medical device 310 but they may also be included in any of 110, 150, 310, or any combination thereof.

Medical device 310 can include any type of device or system with a communications interface that characterizes one or more physiological measurements of a patient and/or that characterize or are used for the treatment of a patient. In some cases, the medical device 310 communicates via peer to peer wired or wireless communications with a modular medical device system 110, a server, or another medical device 310.

Each medical device 310 can include a power source 156 such as a battery or a wired connection to an external power source. In some implementations, such as a modular medical device 150, power source 156 may power a medical device module 150 when inductive receiver 152 is unable to power the medical device module 150. Medical device 310 and modular medical device system 110 may be powered by a battery or an external power source. In one scenario, the medical device module 150 is an infusion pump that is associated with (and fluidly communicating with) a patient. If the patient is moved to another location (e.g., to an x-ray room which is away from inductive backplane 110), then the medical device module 150 must also move with the patient away from inductive backplane 120 in order to continue the current infusion without interruption. At a certain distance from inductive backplane 120, inductive receiver 152 cannot be energized by inductive backplane 120 and therefore cannot power the medical device module 150. In other cases, the inductive backplane 120 may be turned-off or operating in a mode not allowing the inductive receiver 152 to be energized. Accordingly, power source 156 is able to provide the requisite power for the medical device module 150. In one variation, the power source 156 is a battery that can keep the medical device operational in a range of about two to ten hours. It is noted that when a medical device is reattached to the prior inductive backplane or a different inductive backplane, information required to continue the infusion stored in memory 157, without interruption, can be transmitted from the medical device module 150 to the backplane (and to the control unit 140).

In some implementations, the medical device module 150/medical device 310 operate in at least three power states; a fully-off state, an active-off state, and a fully-on state (sometimes referred to as simply an "on state"). In the fully-off state, the module 150/medical device 310 appears to be powered down (dark display, no response to user input, no response noises, etc.), but a low-power processor continues to operate in order to monitor the internal states of the module 150/medical device 310. The low-power processor determines when to initiate a transition to the active-off state based on a timer, an accelerometer, and a power source status monitored by the low-power processor. When the low-power processor determines to initiate a transition to the active-off state, the low-power processor causes one or more data processors in the module 150/medical device 310 to become active by powering them up or waking them from a sleep state. In the active-off state, the module 150/medical device 310 still appear to a user/patient to be fully-off with no displays, lights, audio, and unresponsive to user actions (except the "on" button"). The one or more data processors have networking capability and can contact a server to determine whether there are updates waiting, or whether data should be sent to the server. The one or more data processors can also update the location of the module/medical device 310 from a real time location system (RTLS). Updates to executable code and configuration information can be transferred from the server to the medical device 310 while the medical device 310 is in the active-off state, and/or from the server to the module 150 while the module 150 is in the active-off state. If the "on" button on the module/system is pressed, the low-power processor initiates a transition from either the fully-off state or the active-off state to the fully-on state. In the fully-on state the low-power processor and the one or more data processors are active, the display is on, and the module 150/medical device 310 will interact with a user.

A medical device 310/medical device module 150 can also include low-power processor 340 and data processor(s) 158. The low-power processor 340 consumes a small enough amount of power that the low-power processor may remain on even when the medical device is in the fully-off state (with the display off, indicators off, audible sounds off). The low-power processor 340 can be used to monitor the states of the medical device 310, 150 including the power source status 330. For example, the power source status includes information about whether the medical device 310/medical device module 150 is plugged-in to an external power source, and/or the charge status of the battery. The monitored states can also include whether the medical device 310, 150 is being physically moved using information from accelerometer 350. The medical device 310, 150 may also have a timer 360 facilitating the periodic wake-up of the data processor(s) 158 and/or communications interface 159. To wake-up the medical device 310, 150 means to exit the fully-off state and enter the active-off state where one or more of the data processor(s) 158 and associated memory 157, and communications interface 159 may enter an operational state. If the medical device 310/medical device module 150 is not plugged-in to an external power source, the frequency of periodic wake-up of the medical device 310/medical device module 150 may be selected to be less frequent in order to conserve battery power.

The medical device 310, 150 may include data processor(s) 158 for use in the operation of the medical device in a clinical setting. However, in some implementations, the low-power processor 340 performs all the functions needed in the medical device 310, 150 without the need for data processor(s) 158.

A medical device 310, 150 can include memory 157 that can store executable code for execution by the low-power processor 340 and the data processor(s) 158. The memory 157 can also store data relating to the operation of the medical device 310, 150 such as data characterizing how the medical device is used and parameters relating to same (e.g., number of hours operated, thresholds for alerts, etc.), performance and status information, and well as other aspects relating to the use of the medical device 310, 150 such as patient data, medication administration data, patient treatment parameters, etc. Some or all of the data relating to the operation of the medical device 310, 150 may be configuration information.

As used herein, configuration information is any information that is modifiable by a system user such as information modifiable by the customer, hospital, administrator, nurse, physician, pharmacy, network administrator, and so on. Configuration information can include clinical data sets, international language texts, and syringe lists. Clinical data sets may include patient treatment information and other information. International language texts can include text strings used in the menus and settings of the user display such as display unit 130 or a display incorporated into medical device 150. Syringe lists include compatible syringes with a medical device such as an infusion pump 150A, 150B, or syringe pump 150D. Different medical devices may have different configuration information.

Each medical device 310, 150 can include an additional communications interface 159 other than the optical data transceiver 154 (in some variations the optical data transceiver 154 may not form part of the medical device 310, 150 and so the communications interface 159 may be the only gateway for communication outside of the medical device module 310, 150). This communications interface 159 can be fixed and/or wireless and can be used to communicate to computer networks and peer-to-peer pairing with other devices when the medical device 310, 150 is not coupled to the backplane 120.

In some implementations, the communications interface 159 can be used in addition or instead of the optical data transceiver 154 when the medical device module 150 is coupled to the backplane 120. For example, the medical device module 150 can be seated on the backplane 120 but not have an optical data transceiver. In such a scenario, the communications interface 159 can wirelessly communicate with the control unit 140 of the modular medical device system 110 so that the operation of the medical device module 150 can be monitored and/or controlled by the modular medical device system 110 (whether or not the medical device module 150 is seated). Various types of wireless communications can be used (for this and other aspects described herein) such as short distance protocols such as BLUETOOTH, near field communication (NFC), WiFi, ZIGBEE, and the like.

As noted above, the system 110 comprises a control unit 140 which in turn can comprise at least one data processor and memory for storing instructions for execution by the at least one data processor and/or data characterizing or otherwise relating to the operation of medical device modules 150. The control unit 140 can act to individually monitor and/or control the operation of the medical device modules 150 affixed to the backplane 120 and stand-alone medical devices 310 such that the functionality of the medical device modules 150/medical devices 310 is improved. In some cases, the control unit 140 can orchestrate the operation of multiple medical device modules 150/medical devices 310. For example, certain sequences of operation and/or concurrent operation can be defined amongst the medical device modules 150/medical devices 310. Such an arrangement can permit, for example, coordinated infusion from different fluid sources. Some medical device modules 150/medical devices 310 can function independently from the control unit 140. However, the modules 150/medical devices 310 acquire more complex abilities and functionality when operating under the command and coordination of the controller 140.

In some clinical settings, backplane 120 can be utilized to serve a single patient. With such an arrangement, each inductive backplane 120 can have local communication with other inductive backplanes 120 serving the same patient to provide coordination of operation and shared data. The communication can be wired and/or wireless using, for example, short range digital radio technology, WiFi, optical data transceivers, BLUETOOTH, ZIGBEE, NFC, and the like.

In some implementations, modular medical device system 110 communicates with medical device modules 150 utilizing a communications protocol different from the optical sub-systems (124, 125, 126, 142). For example, in some variations, the inductive transmitters 122 and inductive bus 123 can be used to exchange data with the inductive receiver 152 to affect a near-field magnetic induction communication system. Such an arrangement can provide a short range wireless physical layer that communicates by coupling a tight, low-power, non-propagating magnetic field between the inductive transmitter 122 and the inductive receiver 152. The transmitter coil in the inductive transmitter 122 can modulate a magnetic field which is measured by the inductive receiver 152 in another device. It will be appreciated that the communications are bi-directional and as such, the inductive receiver 152 can also transmit data to the inductive transmitter 122.

In other variations, the modular medical device systems 110 can communicate and exchange data with the medical device modules 150/medical devices 310 via a wireless communications protocol including, but not limited to short range digital radio technology, WiFi, optical data transceivers, BLUETOOTH, ZIGBEE, NFC, and the like.

Figure 4:
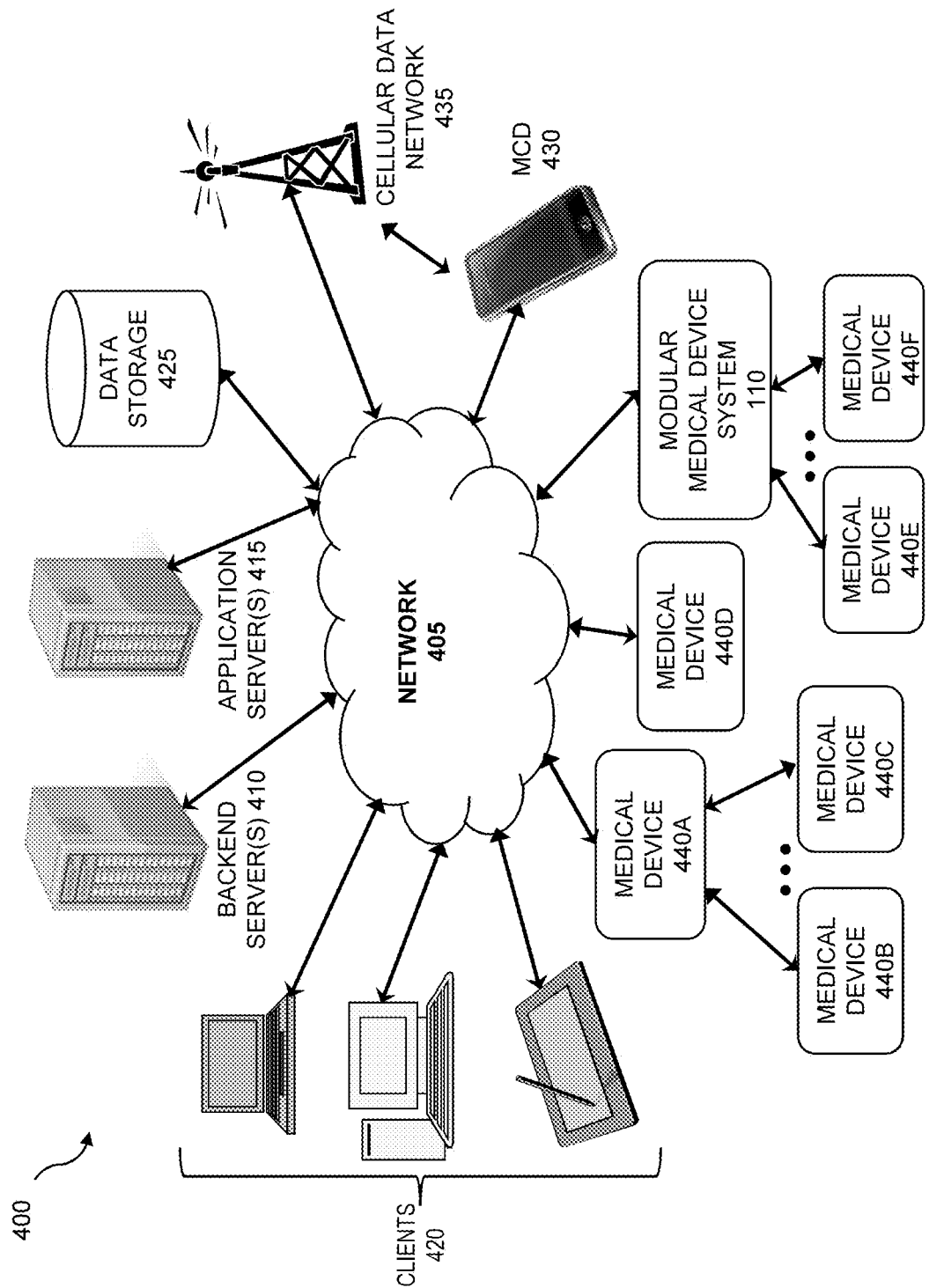
FIG. 4 is a diagram illustrating a computing landscape including a modular medical device system, medical device modules, other medical devices, clients and servers.

FIG. 4 is a system diagram illustrating a computing landscape 400 within a healthcare environment such as a hospital that includes a modular medical device system as well as stand-alone medical devices. Various devices and systems, both local to the healthcare environment and remote from the healthcare environment, can interact via at least one computing network. This computing network can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

The modular medical device systems 110 can include at least one communications interface that can access the computing network 405 either via a fixed wired connection or via a wireless connection (via, for example, one or more access points). In addition, the modular medical device system 110 can also couple to other components within the computing landscape 400 via direct wired or wireless peer-to-peer coupling. Furthermore, in some cases, one or more of the medical devices 440A-D can be self-contained and are not connected to modular medical device system 110. Medical devices 440A-D can be the same or similar to medical devices 310. Modular medical device 150 and medical devices 440A-F can perform the same or similar functions related to providing patient treatment. The modular medical device system 110 can transmit data via the computing network 405 to any of the other components within the landscape 400. In addition, the modular medical device system 110 can receive data from the computing network 405 relating to monitoring and in some cases controlling one or more attributes of the medical device modules 150 and medical devices 440A-F (e.g., software updates, configuration updates, historical data, status information, assets location, patient information, etc.).

In particular, aspects of the computing landscape 400 can be implemented in a computing system that includes a back-end component (e.g., as a data server 410), or that includes a middleware component (e.g., an application server 415), or that includes a front-end component (e.g., a client computer 420 having a graphical user interface or a Web browser through which a user may interact with an implementation of the subject matter described herein), or any combination of such back-end, middleware, or front-end components. Client 420 and servers 410, 415 are generally remote from each other and typically interact through the communications network 405. The relationship of the clients 420 and servers 410, 415 arises by virtue of computer programs running on the respective computers and having a client-server relationship to each other. Clients 420 can be any of a variety of computing platforms that include local applications for providing various functionality within the healthcare environment. Example clients 420 include, but are not limited to, desktop computers, laptop computers, tablets, and other computers with touch-screen interfaces. The local applications can be self-contained in that they do not require network connectivity and/or they can interact with one or more of the servers 410, 415 (e.g., a web browser).

A variety of applications can be executed on the various devices and systems within the computing landscape 400 such as electronic health record applications, medical device monitoring, operation, and maintenance applications, scheduling applications, billing applications and the like. As another example, the applications can comprise a collection of enterprise-based applications that provide dose error reduction software (DERS) for the computing landscape 400 that incorporates a role-based view of infusion data, provides a comprehensive platform for connectivity to external hospital applications, and enables directed maintenance and calibration activities for devices, storage of clinical and device history, etc. As a further example, the applications can provide for remote alarms management and/or asset tracking for medical device modules 150 coupled to one or more of the modular medical device system 110, and for medical devices 440A-F.

The network 405 can be coupled to one or more data storage systems 425. The data storage systems 425 can include databases providing physical data storage within the healthcare environment or within a dedicated facility. In addition, or in the alternative, the data storage systems 425 can include cloud-based systems providing remote storage of data in, for example, a multi-tenant computing environment. The data storage systems 425 can also comprise non-transitory computer readable media.

Mobile communications devices (MCDs) 430 can form part of the computing landscape 400. The MCDs 430 can communicate directly via the network 405 and/or they can communicate with the network 405 via an intermediate network such as a cellular data network 435. Various types of communication protocols can be used by the MCDs 430 including, for example, an internet protocol and messaging protocols such as SMS and MMS. In some cases, the MCDs 430 can receive alerts generated from the operation of the medical device modules 150 coupled to the backplane 120 and/or they can otherwise be used to monitor the operation of such medical device modules 150/medical devices 440A-F.

Various types of medical devices 440 can be used as part of the computing landscape 400. These medical devices 440 can comprise, unless otherwise specified, any type of device or system with a communications interface that characterizes one or more physiological measurements of a patient and/or that characterize or are used for the treatment of a patient. In some cases, the medical devices 440 communicate via peer to peer wired or wireless communications with another medical device 440 (as opposed to communicating with the network 405). For example, the medical device 440 can comprise a bedside vital signs monitor that is connected to other medical devices 440 (and/or the modular medical device system 110), namely a wireless pulse oximeter and to a wired blood pressure monitor. One or more attributes of the medical devices 440 can be locally controlled by a clinician, controlled via a clinician via the network 405, and/or they can be controlled by one or more of a server 410, 415, a client 420, a MCD 430, and/or another medical device 440, or the modular medical device system 110.

The computing landscape 400 can provide various types of functionality as may be required within a healthcare environment such as a hospital. For example, a pharmacy can initiate a prescription via one of the client computers 420. This prescription can be stored in the data storage 425 and/or pushed out to other clients 420, an MCD 430, and/or one or more of the medical devices 440/medical device modules 150. In addition, the medical devices 440/modules 150 can provide data characterizing one or more physiological measurements of a patient and/or treatment of a patient (e.g., medical device 440 can be an infusion management system, etc.). The data generated by the modular medical device system 110 and the medical devices 440 can be communicated to other medical devices 440, the servers 410, 415, the clients 420, the MCDs 430, and/or stored in the data storage systems 425.

Medical devices 440A-F/modules 150, and/or medical device system 110 can contain one or more processors and at least one memory. Executable program code (e.g. software or executable code) is stored in the at least one memory where the executable program code causes the devices 440A-F, 150, 110 to perform operations required for patient care. Configuration information can also be stored in the at least one memory. Configuration information is any information that is modifiable by a system user such as information modifiable by the customer, hospital, administrator, nurse, physician, pharmacy, network administrator, and so on. In order to provide patient care, each of the devices 440A-F, 150, 110 may require a current version of software stored in the at least one memory and may also require a current version of configuration information. Devices 440A-F, 150, 110 may contain multiple processors. Each processor may require current software and configuration information. From time to time, the executable code and/or configuration information of the devices 440A-F, 150, 110 may need to be updated. In some implementations, updates to the executable program code and configuration information are distributed to 440A-F, 150, 110 and deployed within 440A-F, 150, 110 while in the active-off state. In the active-off state, 440A-F, 150, 110 appear to be off to a user/operator. At a clinically appropriate time, the updates can be activated for use by the medical devices 440, 150, and modular medical device system 110. Activation can be performed so that it does not interfere with patient treatment.

As used herein, distribution means to send an update from one device and to receive the update at another device. For example, distribution includes a server sending an update to a modular medical device system (MMDS 110), medical device module 150, or medical device 440. Distribution also includes an MMDS 110 sending an update to a medical device 440 or medical device module 150. Distribution is performed via a communications interface such as communications interface 159, wired or wireless network connection, or optical data transceiver.

To deploy a distributed (received) update to executable code/configuration information means to determine the appropriate processor within the MMDS 110 or medical device 440/module 150 for the received executable code/configuration information update, and to transfer within the MMDS/medical device/module the executable code/configuration information update to the memory or storage associated with the appropriate processor. For example, a medical device module 150 may receive an update to configuration information for one of five processors in the medical device module 150. Deploying the received update within the medical device module 150 transfers the configuration information to storage or memory associated with the appropriate one of the five processors.

To activate a deployed update means to cause the processor to use the deployed update of executable code/configuration information instead of the previously stored version. For example, after an update is distributed from a server to an medical device module 150, and after the update is deployed to a particular processor within the medical device module 150, activation of the update causes the particular processor to use the update when operating.

Activation can occur at a clinically appropriate time selected by the medical device 440/module 150. A clinically appropriate time may be a predetermined time duration after the medical device was turned-off. For example, in some implementations, activation can occur at power-up, when powered-up eight hours after the medical device has been turned off. The time duration required between the when the medical device is turned-off and activation of an update, as well as other conditions required for activation may be part of the updateable configuration information associated with the medical device 440/module 150. In some implementations, patient information is logically discarded eight hours after the device is turned-off which is an opportunity to update without interfering with therapy to a patient. In some implementations, the medical device checks at power-up to see how long the device has been off. At power-up, if the medical device has been off for eight hours or more, the medical device may activate the updated executable code and/or configuration information before becoming available to an operator for use. In some implementations, the medical device may transition from a full-off state to an active-off state to perform an activation which assures that when the device transitions to a fully-on state, the user does not have to wait for the activation to complete (requiring more time than a normal power-up) before becoming available to the operator.

In some implementations, activation is performed when the medical device 440/module 150 is powered-up from a fully-off state. In some implementations, activation is performed as the medical device 440/module 150 is powered-down to a fully-off state. For example, a power switch local to the medical device 440/module 150 may provide a power-down command to the medical device 440/module 150. When an operator presses the switch to initiate powering down, the medical device can first activate deployed updates before completing a power-down process to the fully-off state.

In some implementations, determining a clinically appropriate time to activate an update includes an interaction with the user/operator. For example, an interaction with the user/operator may be needed when activating an update at power-up to a fully-on state or power-down to a fully-off state. The medical device may be powered-up or powered-down for many reasons including to save power when the medical device is not being used, or to reset medical device settings, and so on. To gather more information to use in determining whether to update now or at a later time, the medical device may display one or more messages to the user/operator. For example, the medical device may display a message such as: "New configuration available—update?" or "New patient?" or "Are you finished with this patient?" The response from the user/operator to these and/or other queries may determine whether an update is performed now or at a later time. The answers to these queries allows the medical device to determine if the power-up or power-down was done during a therapy session with a patient. If performed during a therapy session, the medical device may determine to not update now in order to ensure patient information is not changed or discarded during the therapy session, and to ensure the clinical behavior of the medical device remains the same during the therapy session.

Figure 5:
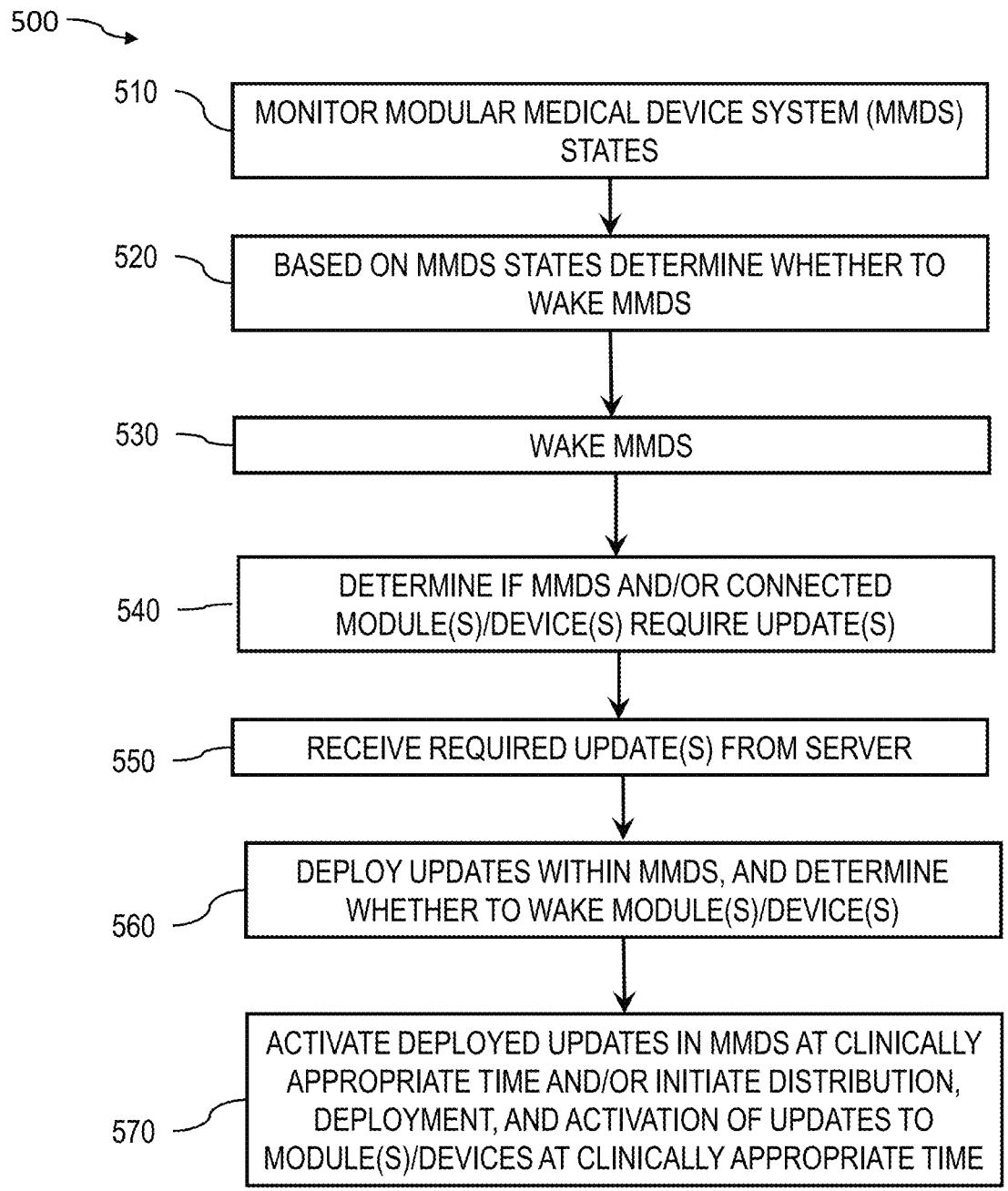
FIG. 5 is an example of a process 500 performed at a modular medical device system to monitor states of the modular medical device system and update executable code and/or configuration information according to the monitored states.

FIG. 5 is an example of a process 500 performed at a modular medical device system (MMDS 110) to monitor the states of the MMDS 110 and update the executable code and/or configuration information in the MMDS 110, and in some implementations update the executable code and/or configuration information in one or more medical device modules/stand-alone medical devices connected to the MMDS 110. At 510, while the MMDS 110 is in the fully-off state and not providing patient treatment or otherwise operational to a user, a low-power processor monitors the states of the MMDS 110. The monitored states include the state of a timer, the state of an accelerometer, and the power source status. Other states may also be monitored. At 520, based on the monitored states, the low-power processor determines whether to wake one or more data processors and memory associated with the one or more data processors, and determines whether to wake a communications interface. At 530, the low-power processor determines to wake the MMDS 110. At 540, the MMDS 110 determines the versions of the executable code and configuration information stored at the MMDS 110, and if one or more updates are available from the server for the MMDS 110. In some implementations, the MMDS 110 also determines the versions of executable code and configuration information stored at one or more medical devices connected to the MMDS 110. At 550, the MMDS 110 receives updates from the server for the MMDS 110 and in some implementations receives updates for the medical devices connected to the MMDS 110. At 560, the received updates for the MMDS 110 are deployed within the MMDS 110. In some implementations, the low-power processor also determines whether to wake the medical devices connected to the MMDS 110. At 570, the updates deployed within the MMDS 110 are activated at a clinically appropriate time. If an update is required at a medical device connected to the MMDS 110, then distribution, deployment, and activation of the update at the medical device may be initiated by the MMDS 110.

At 510, the MMDS 110 is in a fully-off state. The fully-off state is a state where the MMDS 110 is powered down except for a low-power processor 340 or computer. The MMDS 110 appears to a user or patient to be powered down and is not providing patient treatment. The MMDS 110 may not respond to user input and the display may be dark. The MMDS 110 may make no noises or otherwise respond to user/operator input. In the fully-off state the low-power process 340 or monitors the states of the MMDS 110.

The monitored states include the state of the timer 360, the state of the accelerometer 350, and the power source status 330. Other states may be monitored as well. For example, the timer state 360 can be used to periodically wake-up the communications interface 159 to establish a connection to a server such as server 410, 415 and determine if updates are available for the MMDS 110 or for the medical devices 150, 440 connected to the MMDS 110. The timer 360 may provide one or more triggers to wake-up the MMDS 110. The period between timer triggers may be between several hours and several days.

In some implementations, the state of the accelerometer 350 can be used to wake-up the MMDS 110 (to the active-off state) based on motion of the MMDS 110. For example, if the MMDS 110 is in transit from one location to another such as from one hospital room to another, or from one building to another, then the accelerometer may cause the MMDS 110 to wake-up to update a location of the MMDS 110. For example, a real time location system (RTLS) based on information from wireless access points may provide location information to the MMDS 110. Other devices or information may be used to determine location of the MMDS 110 as well. The MMDS 110 may also check server 410, 415 to determine if an update to executable code and/or configuration information is available.

In some implementations, the battery status can be used to determine the wake-up frequency of the MMDS 110. For example, an indication from the power source status 330 that the battery is low may be used by MMDS 110 to determine that the wake-up frequency should be reduced (wake-up less often). In another example, an indication from the power source status 330 that the MMDS 110 has been connected to an external power source or that the battery charge status has improved (e.g. due to charging by an external source) may be used by the MMDS 110 to determine that the wake-up frequency of the MMDS 110 can be increased (wake-up more often). An indication of a very low battery charge may cause a termination of the distribution of an update because the battery may not be able to power the MMDS 110 long enough to transfer the update from the server to the MMDS 110 or from the MMDS 110 to a medical device 440, 150.

At 520, based on the monitored states, the low-power processor 340 determines whether to wake any data processor(s) 158 and memory 157 associated with the data processor(s) 158 in the MMDS 110. The low-power processor 340 also determines whether to wake a communications interface 159.

At 530, the low-power processor 340 determines to wake the MMDS 110 to an active-off state. Waking MMDS 110 may cause one or more of the data processors 158 to begin operation as well as memory supporting the one or more processors 158. Waking may cause communications interface 159 to power-up. Waking the communications interface enables establishing communications between a server such as server 410, 415, or client 420 and the MMDS 110.

At 540, the MMDS 110 or server 410, 415 determines if the MMDS 110 requires one or more updates to executable code or configuration information by determining the current versions of executable code and configuration information being used, and comparing the current versions to the updates available from the server 410, 415. MMDS 110 (or server 410, 415) determines the current version(s) of the executable code and configuration information stored at the MMDS 110. The determination of the versions of the executable code and configuration information at the low-power processor 340 and one or more data processors 158 may be performed via a message exchange between the MMDS 110 and the servers 410, 415 via communications interface 159. In some implementations, servers 410, 415 have a table or list of updated versions of the executable code and configuration information for the low-power processor 340 and data processors 158 in the MMDS 110. The MMDS 110 may have a table or list of the current versions being used at the MMDS 110 of the executable code and configuration information for the low-power processor 340 and on or more data processors 158. The determination of which, if any, low-power processor 340 or data processors 158 require an update may be performed by comparing the versions of executable code and configuration information stored at the processors 340, 158 to the table of updated versions. When an updated version supersedes or is newer than a version stored at one of the processors 340, 158, then the updated version may replace the stored version.

In some implementations, at 540 the MMDS 110 determines if the medical devices 440E-F/modules 150 connected to the MMDS 110 require one or more executable code updates or configuration information updates. In these implementations, the MMDS 110 determines the versions of the executable code and configuration stored at the medical devices 440E-F/modules 150, and the updated versions that are available. The MMDS 110 may have a table or list of updated versions of the executable code and configuration information available for the processors in the medical devices 440E-F/modules 150. The determination of which, if any, of the low-power processor 340 and data processors 158 require updating in each of medical devices 440E-F/medical device modules 150 may be performed by comparing the versions of the stored executable code and configuration information with the table of updated versions. When an updated version in the table stored at the MMDS 110 supersedes a stored version or is newer, then the updated version may replace the stored version at the medical devices 440E-F and/or medical device modules 150.

At 550, the server distributes to the MMDS 110 updates to the MMDS 110. In some implementations, the MMDS 110 distributes updates to the medical devices 440E-F/modules 150 connected to the MMDS 110.

At 560, the distributed updates for the MMDS 110 are deployed within the MMDS 110. In some implementations, the low-power processor 340 determines whether to wake (to an active-off state) the medical device modules 150 and medical devices 440E-F connected to MMDS 110.

At 570, the updates deployed within the MMDS 110 are activated at a clinically appropriate time. If updates are required at the connected medical devices 440E-F/modules 150, then distribution, deployment, and activation of the updates may be initiated by the MMDS 110.

In some implementations, a complete data package containing a complete set of required executable code and a complete set of required configuration information can be provided from server 410, 415, or client 420 to MMDS 110. The complete data package may be all the data that is needed to operate the MMDS 110. In some implementations, a complete data package containing a complete set of required executable code and a complete set of required configuration information can be provided from the MMDS 110 to medical devices 440/modules 150.

In some implementations, server 410, 415, can directly provide executable code updates and/or configuration information updates to a medical device such as medical device 440A and/or 440D via network 405 or other communication method. Medical device 440B and/or 440C can receive executable code updates or configuration information updates from another medical device such as medical device 440A.

Figure 6:
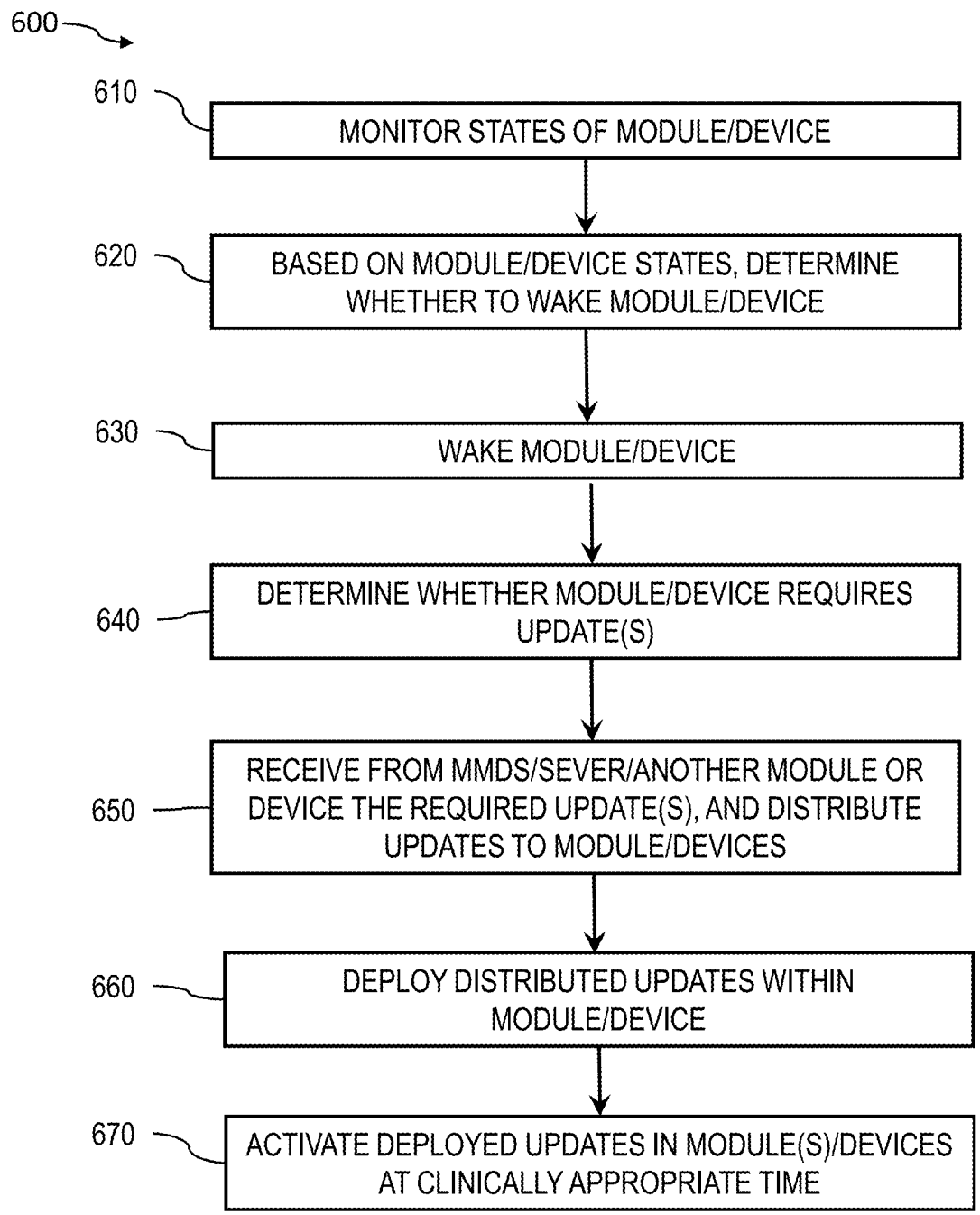
FIG. 6 is an example of a process 600 performed at a medical device to monitor states of the medical device and update executable code and/or configuration information according to the monitored states.

FIG. 6 is an example of a process 600 performed at a medical device module 150 and/or stand-alone medical device 440 (hereafter medical devices 440/modules 150 referred to as medical devices) to monitor the states of the medical device and update the executable code and/or configuration information at the medical device. At 610, while the medical device is in the fully-off state and not providing patient treatment or otherwise operational to a user, a low-power processor monitors the states of the medical device. The monitored states include the state of a timer, the state of an accelerometer, and the power source status. In some implementations, one of the states includes an indication from the MMDS 110 to wake the medical device to an active-off state. Other monitored states are also possible. At 620, the low-power processor 340 determines whether to wake the medical device including any data processor(s) 158 and memory 157 associated with the data processor(s) 158, and determines whether to wake communications interface 159. At 630, the low-power processor 340 determines to wake the medical device. At 640, the medical device determines the versions of the executable code and configuration information stored at the medical device, and if one or more updates are available from the MMDS 110 or servers 410,415. At 650, the medical device receives a distribution from the MMDS 110 (or server) of updates for the medical device. At 660, the distributed updates for the medical device are deployed within the medical device. At 670, the deployed updates are activated at a clinically appropriate time.

At 610, while the medical device is in fully-off state and not providing patient treatment or otherwise operational to a user, a low-power processor 340 monitors the states of the medical device. The fully-off state is a state where the medical device is powered down except for a low-power processor 340 or computer. The medical device appears to a user or patient to be powered down and is not providing patient treatment. The medical device may not respond to user input and the display may be dark. The medical device may make no noises or otherwise respond to user/operator input. In the fully-off state the low-power processor 340 monitors the states of the medical device.

The monitored states include the state of the timer 360, the state of the accelerometer 350, and the power source status 330. Other monitored states are also possible. In some implementations, one of the states includes an indication from the MMDS 110 to wake the medical device. For example, the timer state 360 can be used to periodically wake-up the communications interface 159 to establish a connection to a MMDS 110 and determine if updates are available for the medical device. The timer 360 may provide one or more triggers to wake-up the medical device. The period between timer triggers may be between hours and days.

In some implementations, the state of the accelerometer 350 can be used to wake-up the medical device based on motion of the medical device. For example, if the medical device is in transit from one location to another such as from one hospital room to another, or from one building to another, then the accelerometer 350 may cause the medical device to wake-up to an active-off state to update a location of the modular medical device. For example, a real time location system (RTLS) based on information from wireless access points may provide location information to the medical device. Other devices or information may be used to determine location of the medical device as well. The medical device may also check one or more servers 410, 415 or MMDS 110 to determine if an update to executable code or configuration information is available.

In some implementations, the battery status can be used to determine the wake-up frequency of the medical device. For example, an indication from the power source status 330 that the battery is low may be used by the medical device to determine that the wake-up frequency should be reduced (wake-up less often). In another example, an indication from the power source status 330 that the medical device has been connected to an external power source or that the battery charge status has improved (e.g. due to charging by an external source) may be used by the medical device to determine that the wake-up frequency of the medical device can be increased (wake-up more often). An indication of a very low battery charge may cause a termination of the distribution of an update because the battery may not be able to power the medical device long enough to transfer the update from the MMDS 110 to the medical device or from the server to the medical device.

At 620, based on the monitored states, the low-power processor 340 determines whether to wake data processors 158 and memory 157 associated with the data processors 158 in the medical device. The low-power processor 340 also determines whether to wake a communications interface 159.

At 630, the low-power processor 340 determines to wake the medical device. Waking the medical device may cause one or more of the data processors 158 to begin operation as well as memory supporting the one or more processors 158. Waking may cause communications interface 159 to power up. Waking the communications interface 159 enables establishing communications between the medical device and the MMDS 110 and/or servers 410, 415.

At 640, the medical device or MMDS 110 determines if the medical device requires one or more updates to executable code or configuration information by determining the current versions of executable code and configuration information being used, and comparing the current versions to the updates available from the MMDS 110. The medical device (or MMDS 110) determines the current version(s) of the executable code and configuration information stored at the medical device. The determination of the versions of the executable code and configuration information at the low-power processor 340 and data processors 158 may be performed via a message exchange between the medical device and the MMDS 110 or servers 410,415 via communications interface 159. In some implementations, the MMDS 110 has a table or list of updated versions of the executable code and configuration information for the low-power processor 340 and data processors 158 in the medical device. The medical device may have a table or list of the current versions being used at the medical device of the executable code and configuration information for the low-power processor 340 and data processors 158. The determination of which, if any, of the low-power processor 340 and data processors 158 require an update may be performed by comparing the versions of executable code and configuration information stored at the processors 340, 158 to the table of updated versions. When an updated version is newer or supersedes a version stored at one of the processors 340, 158, then the updated version may replace the stored version.

At 650, the MMDS 110 or server 410, 415 distributes to the medical device updates to the medical device. At 660, the distributed updates for the medical device are deployed within the medical device. At 670, the deployed updates are activated in the medical device at a clinically appropriate time.

In some implementations, activation is performed when the medical device is powered-up from an off state. In some implementations, activation is performed as the medical device is powered-down from an on state. For example, a power switch local to the medical device may provide a power-down command to the medical device. When an operator presses the switch to initiate powering down, the medical device can first activate deployed updates before completing a power-down process.

The following U.S. patent application is hereby incorporated by reference in its entirety: U.S. patent application Ser. No. 13/829,744 entitled "Modular Medical Device System", filed Mar. 14, 2013.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, WiFi (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method comprising:
monitoring, by a low-power processor at a medical device, a power state of the medical device;
determining, by the low-power processor, to periodically wake at least one data processor and memory in the medical device based on the power state, wherein the determining to periodically wake comprises causing the at least one data processor and memory to exit a fully off state by enabling the at least one data processor and memory to operate, wherein the low-power processor and the at least one data processor are different processors, wherein the low-power processor increases a frequency of periodically waking the at least one data processor when the power state indicates that the medical device is attached to an external power source, and wherein the low-power processor decreases the frequency of periodically waking the at least one data processor when the power state indicates that medical device is attached to a battery;
waking the at least one data processor and memory in the medical device;
determining, at the medical device, a first current version of executable code associated with the at least one data processor and a second current version of configuration information associated with the at least one data processor;
polling at least one of a network server and a medical device controller to determine whether at least one of a first update to the first current version of executable code and a second update to the second current version of configuration information are available for the at least one data processor;
receiving the at least one of the first update and the second update from the network server;
deploying the at least one of the first update and the second update to an appropriate one of the at least one data processor; and
activating the at least one of the first update and the second update at a clinically appropriate time, wherein the medical device controller operates in conjunction with the medical device, wherein the clinically appropriate time comprises a time at which the at least one of the first update and the second update will not interfere with patient therapy.

2. The method as in claim 1, wherein the waking comprises enabling to operate at least one communications interface.

3. The method as in claim 1, wherein the executable code comprises at least one of an operating system and an application, and wherein the configuration information comprises values that can be modified by a user, wherein the values affect the functioning of the medical device.

4. The method as in claim 2, wherein the at least one communications interface wirelessly couples the medical device to the network server.

5. A method as in claim 1, wherein the medical device comprises a fluid infusion pump including at least one of: a syringe pump, a patient controlled infusion pump, a large volume infusion pump, and a peristaltic pump.

6. The method as in claim 1, wherein the medical device comprises at least one of a patient-controlled analgesia (PCA) system, a vital signs monitor, a blood analyte monitor, a cardiac output monitors a gastric tonometer, an SpO2 sensor, an EtCO2 sensor, an identification module, a barcode scanner, and a radio frequency identification (RFID) scanner.

7. The method as in claim 1, further comprising:
monitoring, by the low-power processor, a timer of the medical device such that the low-power processor periodically wakes the at least one data processor based on the timer; and
adjusting, by the low-power processor, the timer based on the power state of the medical device.

8. A non-transitory computer-readable medium encoded with instructions that, when executed by a low-power processor, cause operations comprising:
monitoring, by the low-power processor at a medical device, at least one state of the medical device;
determining, by the low-power processor, to periodically wake at least one data processor and memory in the medical device based on the power state, wherein the determining to periodically wake comprises causing the at least one data processor and memory to exit a fully off state by enabling the at least one data processor and memory to operate, wherein the low-power processor and the at least one data processor are different processors, wherein the low-power processor increases a frequency of periodically waking the at least one data processor when the power state indicates that the medical device is attached to an external power source, and wherein the low-power processor decreases the frequency of periodically waking the at least one data processor when the power state indicates that medical device is attached to a battery;

waking the at least one data processor and memory in the medical device;

determining, at the medical device, a first current version of executable code associated with the at least one data processor and a second current version configuration information associated with the at least one data processor;

polling at least one of a network server and a medical device controller to determine whether at least one of a first update to the first current version of executable code and a second update to the second current version of configuration information are available for the at least one data processor;

receiving the at least one of the first update and the second update from the network server;

deploying the at least one of the first update and the second update to an appropriate one of the at least one data processor; and activating the at least one of the first update and the second update at a clinically appropriate time, wherein the medical device controller operates in conjunction with the medical device, wherein the clinically appropriate time comprises a time at which the at least one of the first update and the second update will not interfere with patient therapy.

9. The non-transitory computer-readable medium as in claim 8, wherein the at least one state comprises at least one of a timer state, an accelerometer state, and a power source state.

10. The non-transitory computer-readable medium as in claim 8, wherein the waking comprises enabling to operate at least one communications interface.

11. The non-transitory computer-readable medium as in claim 10, wherein the at least one communications interface wirelessly couples the medical device to the at least one of the network server and the medical device controller.

12. The non-transitory computer-readable medium as in claim 8, wherein the executable code comprises at least one of an operating system and an application, and wherein the configuration information comprises values that can be modified by a user, wherein the values affect the functioning of the medical device.

13. A non-transitory computer-readable medium as in claim 8, wherein the medical device comprises a fluid infusion pump including at least one of: a syringe pump, a patient controlled infusion pump, a large volume infusion pump, and a peristaltic pump.

14. The non-transitory computer-readable medium as in claim 8, wherein the medical device comprises at least one of a patient-controlled analgesia (PCA) system, a vital signs monitor, a blood analyte monitor, a cardiac output monitor, a gastric tonometer, an SpO2 sensor, an EtCO2 sensor, an identification module, a barcode scanner, and a radio frequency identification (RFID) scanner.

15. An apparatus comprising:
a low-power processor; and
a first memory containing executable instructions configured to cause the at least one low-power processor to perform operations comprising:
monitoring, by the low-power processor at a medical device, at least one state of the medical device;
determining, by the low-power processor, to periodically wake at least one data processor and second memory in the medical device based on the power state, wherein the determining to periodically wake comprises causing the at least one data processor and second memory to exit a fully off state by enabling the at least one data processor and second memory to operate, wherein the low-power processor and the at least one data processor are different processors, wherein the low-power processor increases a frequency of periodically waking the at least one data processor when the power state indicates that the medical device is attached to an external power source, and wherein the low-power processor decreases the frequency of periodically waking the at least one data processor when the power state indicates that medical device is attached to a battery;
waking the at least one data processor and memory in the medical device;
determining, at the medical device, a first current version of executable code and a second current version configuration information associated with the at least one data processor;
polling at least one of a network server and a medical device controller to determine whether at least one of a first update to the first current version of executable code and a second update to the second current version of configuration information are available for the at least one data processor;
receiving the at least one of the first update and the second update from the network server;
deploying the at least one of the first update and the second update to an appropriate one of the at least one data processor; and
activating the at least one of the first update and the second update at a clinically appropriate time, wherein the medical device controller operates in conjunction with the medical device, wherein the clinically appropriate time comprises a time at which the at least one of the first update and the second update will not interfere with patient therapy.

* * * * *